United States Patent [19]

Soini

[11] Patent Number: 5,518,883
[45] Date of Patent: May 21, 1996

[54] BIOSPECIFIC MULTIPARAMETER ASSAY METHOD

[76] Inventor: Erkki J. Soini, Krypingintie 20, FIN-21610 Kirjala, Finland

[21] Appl. No.: 193,106

[22] PCT Filed: Jun. 15, 1993

[86] PCT No.: PCT/FI93/00261

§ 371 Date: Feb. 8, 1994

§ 102(e) Date: Feb. 8, 1994

[87] PCT Pub. No.: WO94/01774

PCT Pub. Date: Jan. 20, 1994

[30] Foreign Application Priority Data

Jul. 2, 1992 [FI] Finland ................................. 923065
Oct. 8, 1992 [FI] Finland ................................. 924537

[51] Int. Cl.$^6$ ..................... G01N 33/53; G01N 33/566; C12Q 1/00; C12Q 1/68
[52] U.S. Cl. ................. 435/6; 435/7.1; 435/973; 435/975; 436/501
[58] Field of Search ..................... 435/973, 975, 435/6, 7.9; 436/518, 523, 533, 534, 805, 501

[56] References Cited

U.S. PATENT DOCUMENTS

| 4,923,819 | 5/1990 | Fernandez et al. ................ 436/518 |
| 5,028,545 | 7/1991 | Soini ................................ 436/501 |
| 5,043,265 | 8/1991 | Tanke ............................... 435/6 |

FOREIGN PATENT DOCUMENTS

| 0296136A1 | 12/1988 | European Pat. Off. . |
| WO91/00511 | 1/1991 | WIPO . |

OTHER PUBLICATIONS

Campbell, A. R., "Chemiluminescence: Principles and Applications in Biology and Medicine" Ellis Harwood Ltd, (1988) pages all.
Soini and Lövgren, "Time resolved Fluorescence of Lanthanide Probes and Applications in Biotechnology in: CRC Reviews in Analytical Chemistry", (1987) vol. 18 pp. 105–154.
Hemmilä, I. A., "Applications of Fluorescence in Immunoassays in: Chemical Analysis" J. D. Wine Fordner ed., John Wiley & Sons Inc., 1991, vol. 117 pp. 73–75, 203–218.
Savitsky et. al. Dokl. Nauk. USSR (1,989)304: 1005.

*Primary Examiner*—Toni R. Scheiner
*Assistant Examiner*—Patricia A. Duffy
*Attorney, Agent, or Firm*—Ronald J. Kubovcik

[57] ABSTRACT

The invention relates to a biospecific multiparameter assay method based on the use of different categories of microspheres representing different analytes to be assayed, said categories comprising different amounts of an internal fluorescent dye with short decay time, each category of microspheres being coated with a different biospecific reactant. The method comprises pooling the different categories of microspheres together in a suspension, adding the sample containing analytes to be assayed, adding a mixture of labelled biospecific reactants, diluting the suspension to reduce the concentration of labelled reactants not bound to the microspheres, and identifying the category of each microsphere on the basis of the strength of the electrical signal resulting from the short decay time fluorescent dye. According to the invention, the label of the biospecific reactant is either a compound generating or catalysing a chemior bioluminescence, or a phosphorescent compound.

5 Claims, 1 Drawing Sheet

BIOSPECIFIC MULTIPARAMETER ASSAY METHOD

This invention relates to a biospecific multiparameter assay method.

Immunoassays are a well-established group of biospecific assays and now widely used in routine diagnostics and research laboratories. Another group of biospecific assays, still being developed, is DNA hybridization assays. Biospecific assays generally employ one or several biospecific reactants (e.g. antibody, DNA probe) and normally one of these reactants is labelled. The labels currently used are radioisotopic, enzymatic, luminescent and fluorescent labels.

In routine diagnostics there is a growing need for multiparameter (multianalyte) analysis. Unfortunately, the current methodology does not allow the use of more than two or three simultaneous labels because the spectrometric separation of the signals from different labels is not sufficiently efficient. The emission spectra of different radioisotopic labels and fluorometric labels have a significant overlapping and consequently they provide inadequate separation of different analytes over a required concentration range.

The purpose of this invention is to improve the methodology for biospecific multiparameter assays.

The invention relates to a biospecific multiparameter assay method based on the use of different categories of microspheres representing different analytes to be assayed, said categories comprising different amounts of an internal fluorescent dye with short decay time, each category of microspheres being coated with a different biospecific reactant, said method comprising the steps of pooling the different categories of microspheres together in a suspension, and adding the sample containing analytes to be assayed, and a mixture of labelled biospecific reactants into the suspension to initiate biospecific reactions between the analytes and the labelled reactants and microsphere-associated reactants, diluting the suspension to reduce the concentration of labelled reactants not bound to the microspheres, exciting the internal fluorescent dye and measuring the strength of the emitted fluorescence, and converting the fluorescence emissions to electrical signals, identifying the category of each microsphere on the basis of the strength of the electrical signal resulting from the short decay time fluorescent dye. The method is characterized by either (i) the label of the biospecific reactant being a compound generating or catalysing a chemi-or bioluminescence reaction, and adding an activator into the suspension, which generates or catalyses chemi-or bioluminescence from the labelled reactants on the surface of the microspheres, to generate luminescence emissions, and measuring the concentration of the analyte on each microsphere on the basis of the strength of the electrical signal resulting from the photon emissions generated by the luminescent label; or (ii) the label of the biospecific reactant being a phosphorescent compound, and measuring the concentration of the analyte on each microsphere on the basis of the strength of the electrical signal resulting from the photon emissions generated by the phosphorescent label.

The term "dye" will be used later systematically in the context to the internal fluorescence of the microspheres. The term "label" will be used later systematically in the context to the labelling of the biospecific reactant. The label is a compound generating or catalysing a chemi- or bioluminescence reaction or a phosphorescent compound.

The luminescent label is activated by adding an activator reagent. The phosphorescent label is activated by a pulsed light source.

The multiparameter assay is performed in suspension of artificially manufactured microspheres, comprising a pool of different microspheres representing different analytes, here called categories. Each category of microspheres is first coated with a specific reactant (antibody, DNA, RNA), i.e. the microspheres function as solid supports for said specific reactant and for the biospecific reaction. The invention combines the use of two sources of signal which generate photon emissions at substantially different times. The first possibility of choice is the combination of fluorescent microspheres and luminescent label. The second possibility of choice is the combination of fluorescent microspheres and phosphorescent label. This invention is particularly related to microphotometric methodology combining fluorescent dye for identification of the category of each individual microsphere representing different analytes and luminescent or phosphorescent label which is used for detecting the concentration of the particular analyte on the microsphere after the biospecific reaction.

Figure 1:
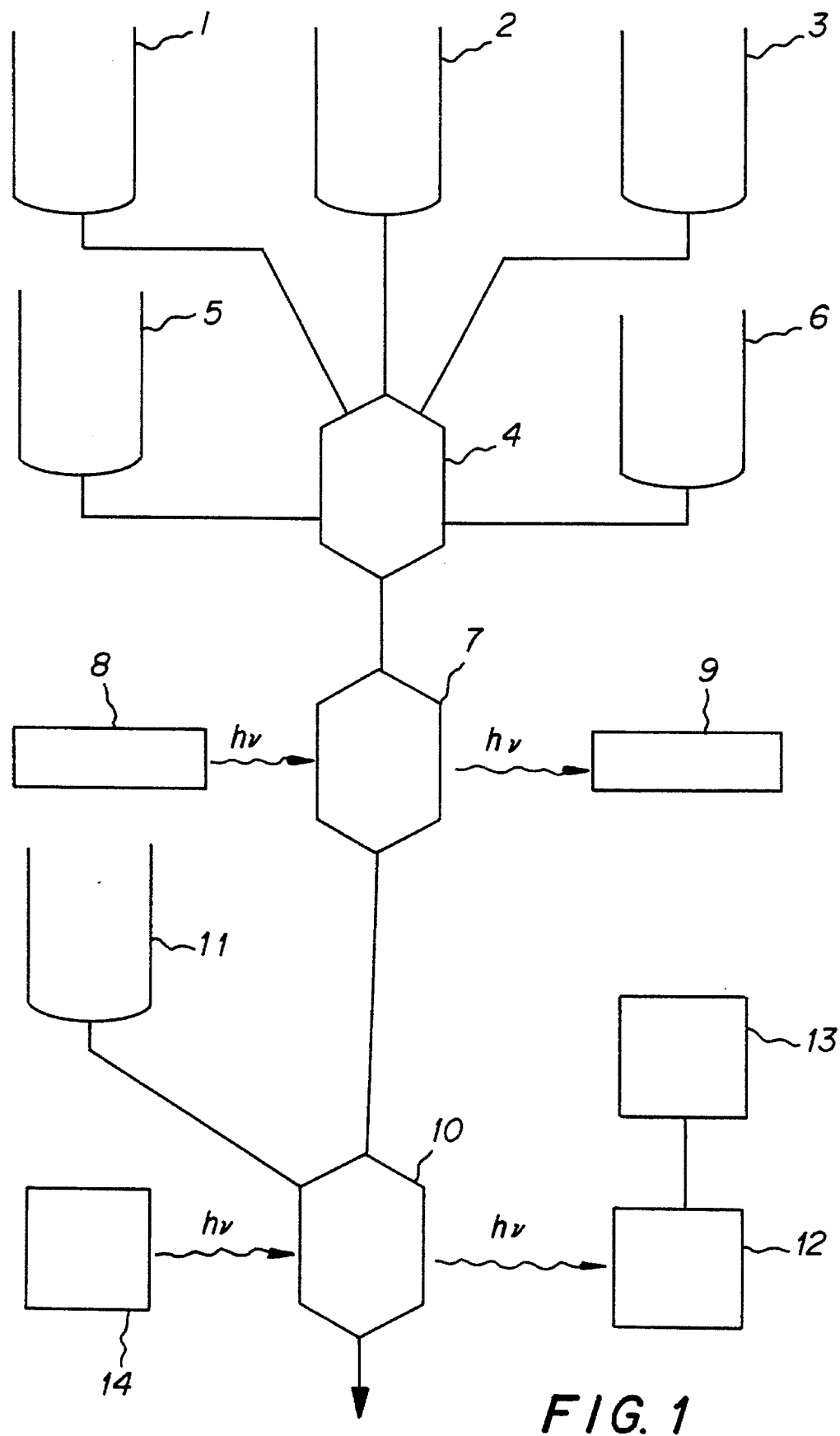
FIG. 1 shows schematically an embodiment of an apparatus for carrying the method according to the invention.

Monosized microspheres with diameter of 1–200 μm (but not limited to this size) can be produced from appropriate polymer material with slight hydrophilic character and therefore they are well suited for water suspensions. The microsphere surface properties allow also binding of macromolecules by physical adsorption as well as by covalent coupling through activation of OH-groups at the surface (L. Johansen et al., J. Immunol. Methods 59, 255–264, 1983). In this invention the sample including all different analytes is first incubated with a pool of microspheres and with a pool of labelled reactants in smallest possible volume (for example 10–100 μl) in order to achieve as complete reaction as possible in a short time. Because of the very small average distance between the analytes molecules and labelled reactants in the microsphere suspension, the equilibrium of the biospecific reaction is achieved rapidly during the incubation and as a result, conjugates consisting of the labelled reactant, the analyte and the immobilised reactant on the microsphere surface, are formed, commonly called "sandwiches" in the literature. After the incubation the suspension is diluted adequately for analysing the individual microspheres with luminometry or phosphorometry. Often a dilution of one order,of magnitude may be enough for sufficiently efficient separation of the bound and free fraction, because the photometric detector used in this invention is able to discriminate optically between those signals originating from the microsphere in the optical focus point and the signal from the free label in the surrounding buffer solution. A sufficient number of microspheres is analysed and the strength of the signal from the label of each microsphere is registered in a computer.

Fluorescent microspheres can be manufactured combining the polymer material with a suitable short decay time fluorescent dye. Fluorescent dyes with very short decay time, for example POPOP, bisMSB, fluorescent lanthanides, fluorescent inorganic microcrystals, fluorescein or rhodamine etc., can be added to any monomer (as discussed e.g. in "Theory and Practice of Scintillation Counting", Ed. J. B. Birks, Pergamon Press, 1967, pp. 321–353) and solid fluorescent material is formed in polymerisation. The material is processed into microspheres in the same step. The fluorescent dyes can alternatively be impregnated into the surface of the microparticles or coupled on the surface of the microparticles. Although the dye in this case is not evenly distributed in the particle, the term "internal" shall be understood to cover this case, too. The fluorescent dye is added into different batches of the monomer in substantially different concentrations differing e.g. by a factor of two from each other. It is important that the fluorescent dye chosen has an absorption band which does not overlap with the emission band of the luminescent or phosphorescent label.

Certain multiparameter biospecific assay methods have been introduced earlier. In most cases, however, the multiparameter methodology has been based on the use of solid substrates with spatially and optically separate reactive areas which are coated with different biospecific reactants (see e.g. PCT WO 84/01031). Multiparameter assay methods based on the use of artificially produced microspheres have also been published. In these methods the identification of the analyte category is based on the use of microspheres of different sizes or of different colours for different categories and the identification takes place by measuring optically the diameter or the absorbance of the particle. U.S. Pat. No. 5,028,545 describes a method, where a fluorescent dye with short decay time is used for identification and another fluorescent compound with long decay time is used for labelling the biospecific reactant. This invention, however, differs from the latter, because the detection of the biospecific reaction in this invention is based on the use of luminescent labels and luminometry or phosphorescent labels and phosphorometry.

The luminescent labels associated with the biospecific reactants at the microsphere surface are based on the use of optimal concentrations of those reactants and the necessary cofactors and accessory enzymes. Either chemiluminescent (such as peroxidase—luminol) or bioluminescent (such as luciferase—luciferin) reactions can be utilised. Luciferases, either of prokaryotic (from species Vibrio, Photobacterium, Xenorhabdus etc.) or of eucaryotic (such as *Photinus pyralis, Pyrophorus plagiothalamus, Lampyris noctiluca, Pholas dactylus, Vargula hilgendorfii*, etc.) origins can be titrated together with their substrates (luciferins), necessary coenzymes and additional enzymes to produce light emission signal that is rather a flash than of constant light producing type. Also optimal amounts of photoproteins such as aequorin, obelin, pholasin or ophiophilisin can be used. Peroxidases or oxidases can be used together with compounds such as luminol or acridines (for instance lucigenin) to yield luminescent signals suitable for a detection system described here. These systems together with enhancers and modulators (wavelength, emission kinetics etc.) of light emission have been described in more detail in Campbell, A. "Chemiluminescence; principles and applications in biology and medicine", Weinheim; Deerfield Beach, Fla.; VCH; Chichester: Horwood, 1988. Enzymatically generated chemiluminescence offers greater sensitivity and rapid detection in immunoassays and in DNA/RNA probe assays. Thermally stable dioxetanes (such as AMPPD and Lumigen PPD) can be chemically and enzymatically (such as alkaline phosphatase or beta-galactosidase) triggered to produce chemiluminescence (Schaap et al., 1989, Clin. Chem., 35, 1863–64). It should also be emphasised that luciferases or photoproteins described above can be fused by recombinant DNA—techniques to IgG-binding protein A or G (Nilsson, B. & Abrahamsen, L., in Methods Enzymol., vol. 185, pp. 144–161, 1990) or directly to specific recombinant antibody proteins such as single-chain antibodies (see Chiswell & McCafferty, TibTech, 10, 80–84, 1992) thus further enhancing the applicability of the method.

The alternative phosphorescent labels associated with the biospecific reactants at the microsphere surface are based on the use of phosphorescent compounds which have a long decay time. Using pulsed light excitation and a time-resolved detection method the signal generated by the phosphorescent label can be measured with high sensitivity and with large dynamic range and efficiently separated from the signal generated by the short decay time fluorescent dye. The efficient separation is based on the fact, that the emissions take place at substantially different times. The decay time of the fluorescent dye is typically in the order of nanoseconds and the decay time of the phosphorescent dye is in the order of milliseconds.

The time resolved measuring principle and the device needed for detection of the phosphorescence is essentially similar to the device normally used for detection of long decay time fluorescence (E. Soini & al. Clin. Chem., 29/1 (1983) 65). Phosphorescence is a phenomenon where the photon emission is originated from the excited states of the molecular electron orbitals as it is the case in fluorescence too, but the photon emission of phosphorescence is generated by the decay of the triplet states whereas the fluorescence emission is generated by the decay of the singlet states. These phenomena and processes are seen clearly as different in the scientific literature and the compound providing such emissions have different structures and physicochemical properties. A large number of phosphorescent compounds are known but normally they are solid or useful only at low temperatures. For this reason these compound have not been used for labelling of biomolecules. Certain metalloporphyrins, however, have been found to be phosphorescent at room temperature and in organic solvents (M. P. Tsvirko & al., Optical Spectroskopia 34, 1094–1100, 1973). Platinum-coroporphyrin and palladium-coproporphyrin have been recently found to emit phosphorescence in water solution, if these compounds are protected with a detergent for the quenching of the water and oxygen. Consequently an idea and a possible method has been introduced for their use for labelling of biomolecules (A. P. Savitsky & al, Dokl. Acad. Nauk. USSR, 304, 1005, 1989). Oxygen is a strong quencher of triplet states but it can be eliminated from the measuring solution using an oxygen binding agent. A simple example of such an agent is sodium sulogute (Savitsky & al. USSR patent no. 4201377). The advantage of porphyrins if compared with lanthanide chelates, is the strong absorbance of the excitation light in the range of 380–400 nm, whereas lanthanide chelates, have their absorption and excitation on the UV-range between 280 and 360 nm. The latter requires special optics and leads to more expensive instrumentation. The emission wavelength range of platinum-coproporphyrin and palladium-coproporphyrin is 640–670 nm.

The invention will be described more in detail with reference to the accompanying drawing. FIG. 1 shows schematicalty an embodiment of an apparatus for carrying the method according to the invention into effect. For liquid processing appropriate valves and pumps are needed. These are, however, not shown in the FIG. 1. The fluorescent microspheres in different categories, representing different analytes, are coated with primary biospecific reactants (antibodies, DNA etc.) and are pooled together in a suspension in the container 1. A 10 µl aliquot of the sample (e.g. blood serum) 2 and a 10 µl aliquot of the secondary biospecific reactant labelled with luminescent label or with phosphorescent label 3 are injected into reaction chamber 4 and incubated at an appropriate (e.g. 37° C.) temperature for a precisely controlled period of time (e.g. several minutes or longer). The suspension of the microspheres is then diluted and washed with the buffer solution (e.g. 100 mM Na-K-phosphate, pH 7.4, 0.9% NaCl, BSA 1 mg/ml) taken from the container 5. During this washing step the microspheres are immobilised in the reaction chamber by a filter membrane, magnetic forces or by any other means. The suspension of the microspheres is then transferred to a capillary fluorescence detection chamber 7 illuminated with monochromatic light source 8 for determination of the category of the microsphere on the basis of the signal strength of the short decay time fluorescent dye obtained from the fluorescence detector 9. Then the suspension is conducted to a capillary detection chamber 10 with an aliquot of an activator solution 11 which functions as an activator of the luminescent reaction or as an enhancement agent of the phosphorescent label. The concentration of the analyte associated with the microspheres is the measured by determination of the signal strength from the luminescent label or from the phosphorescent label. The emitted photons are detected by the photon counter 12 which is optically coupled to the detection chamber 10. The photons are registered with the electronic counting device 13.

In the case of a luminescent label, the secondary reagent may be labelled with biotin and consequently there is a need to add streptavidin labelled covalently with e.g. firefly luciferase into reaction chamber 4 in order to convert the labelled reagent to a form appropriate for luminescent reaction. Many other luminescent reactions used for detection may need a similar additional step. The luminescence requires activation with injection of the luminescence activator and in this case the activator solution 11 contains luciferin, i.e. the substrate of the firefly luciferase (e.g. 0.1M TRIS-Cl, pH 7.75, 0.1 mM D-Luciferin, 0.1 mM ATP, 1 µM pyrophosphate, 1 mM $MgCl_2$ and 1 µM coenzyme A).

In case of a phosphorescent label, the labelled secondary reagent may need an enhancement agent (e.g. buffer solution of pH 7.2–7.4 containing 4 mg/ml sodium sulphite and 1% Triton X-100) taken from container 6 or 11 which is used to optimise the condition for maximal signal strength and minimum quenching of the phosphorescence emission. The detection chamber is illuminated with a pulsed light source 14 and the emitted photons are detected on 640–670 nm range and registered with the electronic counting device 13 incorporating a time-resolved counting function. The detection chambers 7 and 10 can alternatively be combined into one single physical unit.

In both cases the detection of the analyte concentration in the microspheres takes place measuring the signal strength of the photon emission using a photomultiplier tube or any other appropriate photon detector or image detector (CCD). The capillary detection chambers 7 and 10 may also be combined in one unit. In addition the analysis of the microspheres can be performed in a stationary state or in a stopped-flow system. A sufficient number of randomly flowing microspheres are identified and analysed in order to obtain a sufficient amount of information for desired statistical precision for each analyte.

The microphotometric detection can discriminate between the microsphere-associated emission and solution-associated emission, because the respective concentrations in the microphotometric focal point and in the diluted suspension differ by many orders of magnitude. This detection concept provides a reasonable separation of the free and the bound fractions but, if necessary, it can be made more efficient using normal separation methods (washing, filtration, centrifugation etc.).

The method relative to this invention combines the features referred to above and the device performing the functions can be realised in many different ways. The objective of this invention is to identify each individual microsphere representing different analyte categories for the purpose to perform a multiparameter assay in the same sample. The identification is based on detection of fluorescence as discussed above. In an appropriate measuring system, the short decay time fluorescence of the internal fluorescent dye and the signal from the label can be separately detected because they occur at different times. In particular, when the decay time of the short decay time fluorescence is in the order of nanoseconds, the emission signal is completely decayed when luminescence reaction is activated or when the phosphorescence signal is measured. This is the crucial point of this invention and the fast decaying fluorescent material can be used for identification of the categories of the microspheres without any significant interference with the determination of the analyte concentration with luminometry or phosphorometry.

What is claimed is:

1. A biospecific multiparameter assay method based on the use of different categories of microspheres, each different category representing a different analyte to be assayed and comprising an amount of an internal fluorescent dye with short decay time sufficient to provide fluorescence that is measurably different from each other different category, each different category of microspheres being coated with a different biospecific reactant, said method comprising the steps of pooling the different categories of microspheres together in a suspension, and adding the sample containing analytes to be assayed and a mixture of labelled biospecific reactants that bind to the analytes of interest into the suspension to initiate biospecific reactions between the analytes and the labelled reactants and microsphere-associated reactants, diluting the suspension to reduce the concentration of labelled reactants not bound to the microspheres, exciting the internal fluorescent dye and measuring he strength of the emitted fluorescence, and converting the fluorescence emissions to electrical signals and identifying the category of each microsphere on the basis of the strength of the electrical signal resulting from the short decay time fluorescent dye, characterized by the label of the biospecific reactant being a phosphorescent metalloporphyrin and for each identified category of microspheres determining the concentration of the analyte bound to a microsphere of said category by measuring the strength of the electrical signal resulting from the photon emissions generated by the phosphorescent label on said microsphere.

2. The method according to claim 1 characterized in that the internal fluorescent dye is a fluorescent compound with a short decay time.

3. The method according to claim 1 characterized in that the phosphorescent metalloporphyrin platium-coproporphyrin or palladium-coproporphyrin.

4. Assay reagent kit for biospecific multianalyte assay method, characterized in that it comprises a prepared suspension of different categories of microspheres representing different analytes to be assayed, each different category comprising an amount of internal fluorescent dye sufficient to provide fluorescence that is measurably different from each other different category, each category of microspheres being coated with a different biospecific reactant, and a mixture of biospecific reactants that bind to the different analytes to be measured labelled with a phosphorescent metalloporphyrin.

5. The method according to claim 2 wherein the internal fluorescent dye is POPOP or bis-MSB.

* * * * *